United States Patent [19]

McLeod

[11] Patent Number: 5,562,644
[45] Date of Patent: Oct. 8, 1996

[54] METHOD AND APPARATUS FOR THE RELIEF OF HEADACHE PAIN

[76] Inventor: Martha S. McLeod, 905 Paluxy Rd., Apt. 501, Granbury, Tex. 76048

[21] Appl. No.: 396,708
[22] Filed: Mar. 1, 1995
[51] Int. Cl.⁶ ....................................................... A61F 7/00
[52] U.S. Cl. ............................................................. 604/291
[58] Field of Search .............................................. 604/291

[56] References Cited

U.S. PATENT DOCUMENTS 4,765,338  8/1988  Turner ...................................... 128/402

Primary Examiner—Paul J. Killos

[57] ABSTRACT

A method of treating headaches that involves generating chilled air, conveying the air to the patient, and inhaling the chilled air until relief is obtained. Apparatus for generating chilled air for the treatment of headaches that includes a heat exchanger located in an insulated housing, a fan for moving air over the heat exchanger, a conduit connected to the housing for conveying the chilled air to a face mask for inhalation by the patient.

15 Claims, 2 Drawing Sheets

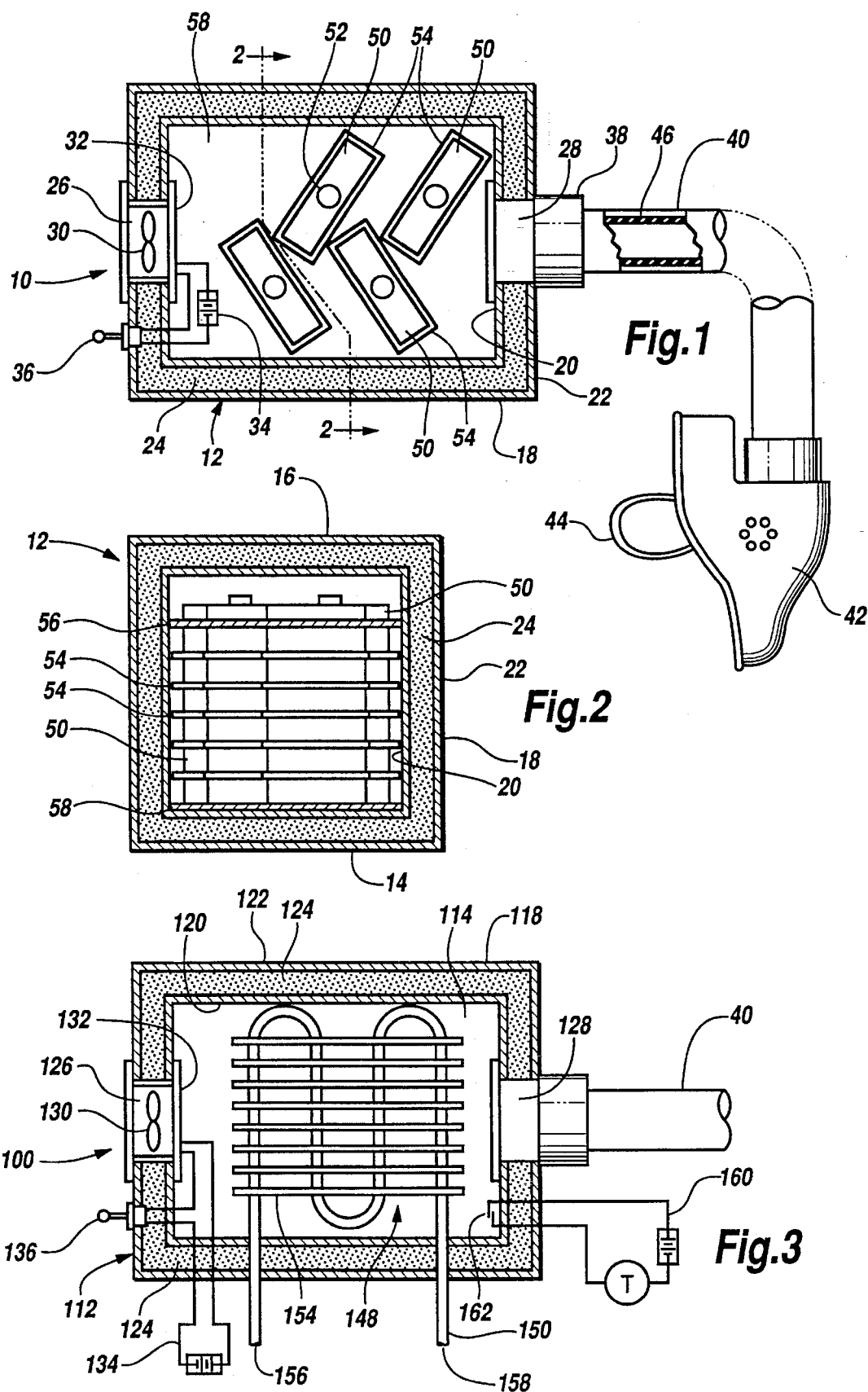

| Subect# | Cold Room Air Degree of Relief | | | | 100% Oxygen Degree of Relief | | | |
|---|---|---|---|---|---|---|---|---|
| | 0 | 1 | 2 | 3 | 0 | 1 | 2 | 3 |
| 1 | 0 | 6 | 4 | 0 | 0 | 4 | 1 | 0 |
| 1 | 0 | 0 | 0 | 10 | 0 | 0 | 0 | 5 |
| 1 | 0 | 1 | 0 | 9 | 0 | 0 | 0 | 5 |
| 1 | 0 | 0 | 2 | 8 | 0 | 0 | 0 | 5 |
| 1 | 0 | 2 | 8 | 0 | 0 | 0 | 2 | 3 |
| 1 | 0 | 0 | 0 | 10 | – | – | – | – |
| 1 | 0 | 3 | 7 | 0 | 0 | 1 | 4 | 0 |
| 1 | 0 | 0 | 2 | 8 | – | – | – | – |
| Total | 0 | 12 | 23 | 45 | 0 | 5 | 7 | 18 |
| Percentage | 0 | 15.0 | 28.8 | 56.2 | 0 | 16.7 | 23.3 | 60.0 |

Number and Percentage of Cases in Which Effective Relief Was/Was Not Obtained

METHOD AND APPARATUS FOR THE RELIEF OF HEADACHE PAIN

FIELD OF THE INVENTION

This invention relates to improved apparatus and method for the treatment of patients suffering from pain caused by headaches. More particularly, this invention relates to an improved method utilizing chilled air to abate headache pain and to portable apparatus for generating chilled air that is inhaled by a patient for the abatement of pain caused by such headaches.

BACKGROUND OF THE INVENTION

Simple headaches produce varying degrees of pain. Generally, such pain can be relieved by treatment with analgesic pain relievers such aspirin and ibuprofen.

More chronic headaches, such as migraine and "cluster" headaches, most often, do not respond to such treatment. Such headaches almost always require very strong medication for their relief if they can be relieved at all.

Patients having the propensity for headaches of these types are prone to repeated attacks that may produce extremely severe pain that sometimes cannot be abated even with the use of the strong medications. Often, the amount of medication required to ease the pain results in side effects that can be a severe as the headaches and may linger for extended periods of time.

In recent years, it has been discovered that relief or abatement of the headache pain can be obtained when the patient inhales one hundred percent oxygen although rebound headaches do sometimes occur. It is not fully understood why the oxygen therapy is effective.

While attempting to determine why the oxygen therapy works, it was determined that chilled air, when inhaled, provides relief or complete abatement as effectively as oxygen and apparently without the rebound headaches. In addition, the chilled air therapy has no side effects and can be made into a light weight, completely portable device.

The chilled air device is simple in construction and use. It requires little maintenance and can be unobtrusively carried into an office, school or the like and used while performing usual personal routines. If desired, more sophisticated chilled air devices can be provided for more or less fixed use, such as in hospitals or in the home.

One of the problems in using the oxygen therapy is the potential for explosion or fire. Smokers are reluctant to use the oxygen therapy because of the danger of fire. Non-smokers are also exposed to the possible danger unless they are extremely careful about where the oxygen is used. Manifestly, the use of oxygen in an office or classroom is prohibited. Thus, the patient suffering from migraine or "cluster" headaches cannot attend class or remain at the office. No such danger exists with the use of the chilled air device and therapy.

Another problem that exists with the oxygen therapy apparatus is that the bottles utilized to hold the compressed oxygen are very heavy due to the pressures involved and may necessarily be rather large because of the volume of gas used in the treatment. A regulator must be used to control the outlet gas pressure adding to the complexity, cost, weight and size of the oxygen device. The chilled air device on the other hand can be extremely small and compact since no compressed gases are used. The device generates the chilled air with little power required and with little noise.

One object of this invention is to provide improved apparatus for the relief of headache pain. Another object of this invention is to provide an improved method for the relief of headache pain.

SUMMARY OF THE INVENTION

In one aspect, this invention contemplates improved apparatus for providing chilled air for the relief of a patient suffering from a headache that comprises a housing having a sidewall with inlet and outlet passageways extending therethrough, a heat exchanger located in the housing, an air circulation fan for air into contact with the heat exchanger, and air conduit having one connected to the outlet passageway, and a breathing mask connected to another end of said conduit and arranged to be placed over the mouth and nose of the patient whereby chilled air is inhaled by the patient.

In another aspect of the invention, an improved therapeutic method for the treatment of headache pain that comprises chilling air, delivering the chilled air to the patient, and inhalation of the chilled air by the patient to relieve the pain.

BRIEF DESCRIPTION OF THE DRAWING

The foregoing and additional objects and advantages of the invention will be more fully understood when the following detailed description is read in conjunction with the accompanying drawing wherein like reference characters denote like parts in all views and wherein:

FIG. 1 is a horizontal cross-sectional view of chilled air generating apparatus that is constructed in accordance with the invention.

FIG. 2 is a vertical cross-sectional view taken generally along the line 2—2 of FIG. 1.

FIG. 3 is a view similar to FIG. 1, but illustrating another embodiment of chilled air generating apparatus that is also constructed in accordance with the invention.

DETAILED DESCRIPTION OF THE INVENTION

Figures 4, 5:
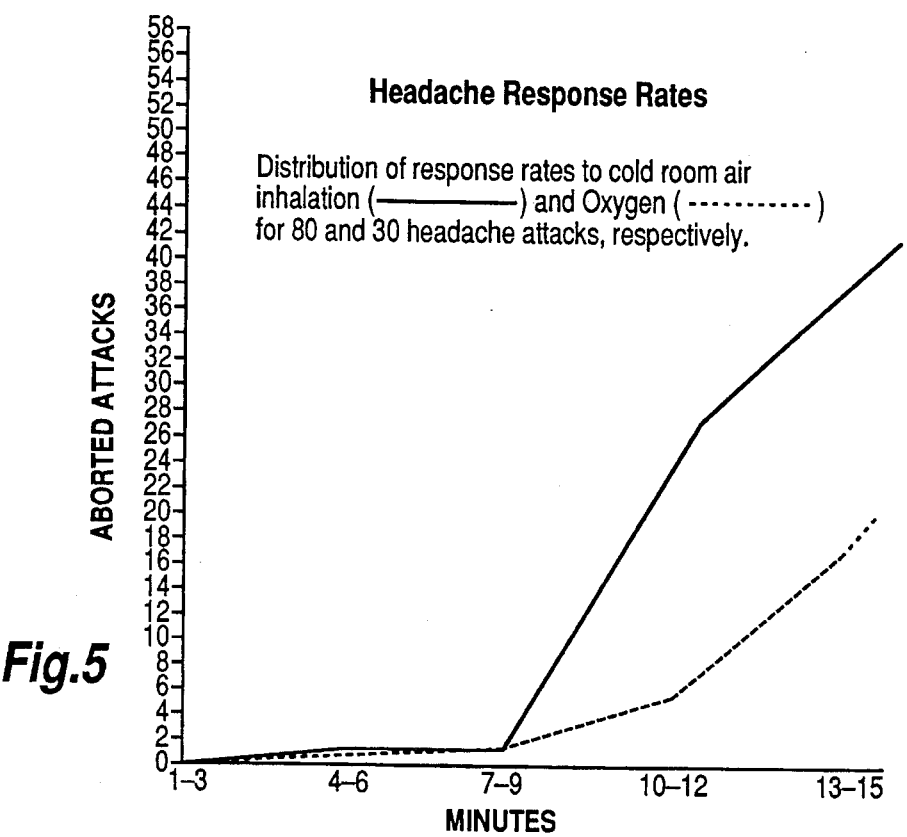
FIG. 4 is chart illustrating a comparison of relief obtained when using the apparatus and method of the invention and when using known oxygen therapy.
FIG. 5 is a graph showing a comparison of headache response times when the treatments illustrated in FIG. 4 are used.

The preferred embodiment of the invention is illustrated in FIGS. 1 and 2. As shown therein, chilled air apparatus 10, when constructed in accordance with the invention includes a hollow housing 12 having a bottom 14, a removable top 16, and a sidewall 18.

The sidewall 18, has inner and outer walls 20 and 22 that are slightly separated to enclose an insulating material 24. Preferably, the top 16 and bottom 14 will be similarly constructed as shown in the vertical cross-sectional view of FIG. 2.

As shown in FIG. 1, the wall 18 has an inlet passageway 26 and an outlet passageway 28 extending therethrough. An electric fan 30 is located in the inlet passageway 26 and is mounted on the housing 12. The fan 30 is arranged to move air through the inlet passageway 26 into the housing 12.

The fan 30 includes a motor 32 that is powered by a battery pack 34. The battery pack 34 is appropriately connected to the motor 32 through a switch 36 that is also mounted on the housing 12 and functions to control the motor 32.

An adapter 38 is located in the outlet passageway 28 for connecting one end of an air conduit 40 to the housing 12. The other end of the conduit 40 is connected to a non-rebreathing face mask 42 the construction of which is well known. The mask is arranged to be placed over the mouth and nose of the patient and releasably secured in such position by an elastic band 44 that is connected to each side of the mask 42.

The conduit 40 is preferably insulated by an insulating layer 46 that encircles the conduit 40 between the housing 12 and the mask 42. The conduit 40 may be of any desired length, but should be long enough to permit the patient to use the apparatus 10 without discomfort.

A heat exchanger 48 includes a plurality of heat exchange members 50 that are positioned in the housing 12 between the inlet and outlet passageways 26 and 28. Each of the heat exchange members 50 is hollow and is filled with a liquid that can be relatively easily frozen. Each may be permanently sealed or provided with a removable cap 52 closing the top thereof. The caps 52 are removable to permit replacement of the liquid when desired.

Each of the heat exchange members 50 also has a plurality of spaced heat transfer fins 54 encircling the exterior thereof. The fins are provided to increase the heat transfer efficiency of the exchange members 50.

The exchange members are held in the desired position in the housing 12 by upper and lower spaced locating members 56 and 58, respectively. Each of the members is provided with apertures located to receive the members 50 and to prevent their movement within the housing 12. The upper member 56 is removably located in the housing 12 so that the members 50 can be easily removed for refilling, cleansing, etc.

To use the apparatus 10, the exchange members 50 with the liquid therein frozen are placed in the housing 12 as shown in FIG. 1. The switch 36 is placed in the "on" position to start the fan 30. Air moved by the fan 30 enters the inlet passageway 26 passing by and between the exchange members 50 where the air is chilled. When the patient dons the mask 42 and begins to breath, the chilled air passes through the outlet passageway 28 into the conduit 40 through which it is delivered to the mask 42. As the patient inhales the chilled air, it is believed that the chilling effect of the air on the membranes over which it passes results in constriction of the blood vessels as well as a possible anesthetic effect. Both effects are believed to be responsible for the relieving of the pain caused by cluster and migraine headaches.

The fan 30, passageway sizes, arrangement of exchange members and flow characteristics have been selected so that when the apparatus 10 is in use the temperature of the chilled air reaching the mask 42 will be between 36 and 42 degrees Fahrenheit or approximately 40 degrees Fahrenheit. Temperatures in this range have been shown to be effective in treating the pain, but not so low as to cause frostbite or other problems to the patient.

The preferred form of the apparatus 10 is completely portable, very light weight, operates quietly so that it can be used virtually anywhere with ease and without disturbing others permitting patients suffering from migraine or cluster headaches to lead a very normal life.

The Embodiment of FIG. 3

The embodiment of the invention illustrated in FIG. 3 is a modified version of the chilled air apparatus 10 that is designated by the reference character 100. When constructed in accordance with the invention the apparatus 100 includes a hollow housing 112 having a bottom 114, a removable top (not shown) and a sidewall 118.

The sidewall 118, has inner and outer walls 120 and 122 that are slightly separated to enclose an insulating material 124. Preferably, the top and the bottom 114 will be similarly constructed as shown in the vertical cross-sectional view of FIG. 2.

As shown in dash lines in FIG. 3, the wall 118 has inlet and outlet passageways 126 and 128 extending therethrough. An electric fan 130 is located in the inlet passageway 126 and is mounted on the housing 112. The fan 130 is arranged to move air through the inlet passageway 126 into the housing 112.

The fan 130 includes a motor 132 that is electrically powered through lead wires 134. The wires 134 are appropriately connected to the motor 132 through a switch 136 that is also mounted on the housing 112 and functions to control the motor 132. Preferably, the motor is driven through a very low voltage circuit(not shown) to eliminate the possibility of dangerous electrical shock. The previously described adapter 38 is located in the outlet passageway 128 for connecting on end of the air conduit 40 to the housing 112. The other end of the conduit 40 is connected to the non-rebreathing face mask 42 the construction of which is well known. The mask is arranged to be placed over the mouth and nose of the patient and releasably secured in such position by elastic band 44 that is connected to each side of the mask 42 as described in connection with the embodiment of FIG. 1.

A heat exchanger 148 includes a sinuous heat exchange tube 150 that is positioned in the housing 112 between the inlet and outlet passageways 126 and 128. The heat exchange tube or conduit 150 has a plurality of spaced heat transfer fins 154 on the exterior thereof. The fins 154 are provided to increase the heat transfer efficiency of the exchange tube 150.

As illustrated, the conduit 150 has an inlet end 156 and an outlet end 158 extending through the wall 112. The ends 156 and 158 are to be connected to chilled water or other refrigerant which will pass therethrough providing for the chilling of the air in the housing 112.

To control the temperature in the apparatus 100, a thermostatic device 160 has been incorporated. A bimetallic element 162 is located within the housing 112 to sense the temperature therein. The structure and operation of a thermostat is well known and will not be described in detail herein.

The apparatus 100 is used and operates identically to the apparatus 10, except that it is not quite as portable as the apparatus 10. The apparatus 100 is more appropriately used in fixed or virtually fixed situation, such as in the home or in the hospital.

Tests have been run using apparatus constructed virtually as described in connection with FIGS. 1 and 2. The tests were also comparative in that tests were also run using the oxygen therapy.

During the tests, the patients were asked not to take a prophylactic medication. The cold air treatment was self administered by the patients in their homes.

At the onset of a headache, the patients were asked to note the time of onset, to place the apparatus on the table, and to sit comfortably upright in front of the apparatus. The patients inhaled only slightly deeper than normal and breathed at their normal rate. Inhalation continued until the headache was aborted or until 15 minutes had elapsed, whichever came first. (If the headache was not aborted the patient was allowed to use the usual mechanism for relief.)

The level of relief obtained was graded on a Likert Scale from 0 to 3 with 2 being substantial relief and 3 being complete relief. Ten headache attacks were scored for each patient.

Six of the patients studied using chilled air had previously used oxygen therapy. They were asked to report on their use of oxygen therapy for five additional headaches so that a comparison could be made between the oxygen and chilled air methods.

The results of the tests indicate that the chilled air method was effective 85% in relieving cluster headaches and ineffective 15%. The results of the tests using oxygen therapy indicate that that method is effective 83% and ineffective 17%. The level of relief results where that the chilled air method produced a mean score of 2.69 while the oxygen method produced a mean score of 2.72. FIG. 4 illustrates the results of the tests with respect to relief and to degree or level of relief The tallies of the rate of response to the two methods indicate that the chilled air method required inhalation between 6 and 15 minutes. The oxygen method required inhalation between 7 and 15 minutes. Headache response rate results are illustrate in FIG. 5.

From the foregoing, it can be concluded that the chilled air method for obtaining headache relief is at least as effective as the oxygen method. It should be remembered that the chilled air method may utilize the safe, completely portable apparatus described in detail hereinbefore. The problems of drug side effects are avoided as well as avoiding the potential hazards related to the use of 100% oxygen.

What I claim is:

1. Apparatus for providing chilled air for the relief of headaches, said apparatus comprising in combination;

a housing including a top, a bottom, and a sidewall extending between said top and bottom, said sidewall having inlet and outlet passageways extending therethrough;

heat exchange means located within said housing arranged to chill air passing through said housing;

air circulating means for moving air through said inlet passageway in said housing into contact with said heat exchange means;

an air conduit having one end connected to said outlet passageway in said housing and having a second end;and, a breathing mask connected with the second end of said conduit, said mask being arranged to be placed over the mouth and nose of the headache patient whereby chilled air is inhaled by the patient for the relief of the headache.

2. The apparatus of claim 1 and also including temperature control means maintaining the temperature of the chilled air to between thirty six and forty two degrees Fahrenheit.

3. The apparatus of claim 1 and also including temperature control means maintaining the temperature of the chilled air to about forty degrees Fahrenheit.

4. The apparatus of claim 1 wherein said air circulating means includes:

a fan; and, an electrically powered motor mounted on said housing for driving said fan.

5. The apparatus of claim 1 wherein said air circulating means includes:

a low voltage power source located in said housing connected to said motor for providing power to said motor; and, a switch operably connected between said low voltage power source and said motor for controlling said motor.

6. The apparatus of claim 5 wherein said low voltage power source includes at least one battery.

7. The apparatus of claim 5 wherein said low voltage power source includes a transformer having an alternating current input for connection to a source of electrical power and a direct current output connected to said motor and switch.

8. The apparatus of claim 1 wherein said heat exchange means includes a plurality of hollow members arranged in said housing to impede the flow of air from said inlet passageway to outlet passageway, each said hollow member containing a liquid that can be chilled.

9. The apparatus of claim 8 wherein each said hollow member is provided with a plurality of spaced radiating fins on the exterior thereof.

10. The apparatus of claim 1 wherein said heat exchange means includes a coolant conduit extending sinuously through a plurality of spaced radiating fins, said conduit and fins located in said housing and having a coolant inlet and outlet extending through said housing wall.

11. The apparatus of claim 8 and also including removable mounting means located in said housing releasably holding said hollow members in position in said housing, whereby said hollow members can be easily removed from said housing for chilling.

12. Apparatus for providing chilled air for the relief of headaches, said apparatus comprising in combination;

a housing including a top, a bottom, and a sidewall extending between said top and bottom, said sidewall having inlet and outlet passageways extending therethrough;

heat exchange means located within said housing arranged to chill air passing through said housing, said heat exchange means including a plurality of hollow members arranged in said housing to impede the flow of air from said inlet passageway to outlet passageway, each said hollow member containing a liquid that can be chilled and provided with a plurality of spaced radiating fins on the exterior thereof;

removable mounting means located in said housing releasably holding said hollow members in position in said housing, whereby said hollow members can be easily removed from said housing for chilling;

air circulating means for moving air through said inlet passageway in said housing into contact with said heat exchange means, said air circulating means including a fan and a battery powered motor mounted on said housing for driving said fan;

an air conduit having one end connected to said outlet passageway in said housing and having a second end;and, a breathing mask connected with the second end of said conduit, said mask being arranged to be placed over the mouth and nose of the headache patient whereby chilled air is inhaled by the patient for the relief of the headache.

13. The apparatus of claim 12 wherein said air conduit and housing are insulated to maintain the temperature of the chilled air.

14. Apparatus for providing chilled air for the relief of headaches, said apparatus comprising in combination;

a housing including a top, a bottom, and a sidewall extending between said top and bottom, said sidewall having inlet and outlet passageways extending therethrough;

heat exchange means located within said housing arranged to chill air passing through said housing, said heat exchange means includes a coolant conduit extending sinuously through a plurality of spaced radiating fins, said conduit and fins located in said housing and having a coolant inlet and outlet extending through said housing wall;

air circulating means for moving air through said inlet passageway in said housing into contact with said heat exchange means, said air circulating means including a fan and an electrically powered motor mounted on said housing for driving said fan;

a low voltage power source connected to said motor for providing power to said motor;

a switch operably connected between said low voltage power source and said motor for controlling said motor;

an air conduit having one end connected to said outlet passageway in said housing and having a second end;

a breathing mask connected with the second end of said conduit, said mask being arranged to be placed over the mouth and nose of the headache patient whereby chilled air is inhaled by the patient for the relief of the headache;and, temperature control means for maintaining the temperature of the chilled air to between thirty six and forty two degrees Fahrenheit.

15. The apparatus of claim 14 wherein air conduit and housing are insulated to maintain the temperature of the chilled air.

* * * * *